(12) United States Patent
Cali et al.

(10) Patent No.: US 8,632,493 B2
(45) Date of Patent: Jan. 21, 2014

(54) RETRACTABLE SYRINGE

(75) Inventors: Ross J. Cali, Eight Mile Plains (AU); Aaron Rodd, Burleigh Waters (AU)

(73) Assignee: Medigard Limited (AU)

(*) Notice: Subject to any disclaimer, the term of this patent is extended or adjusted under 35 U.S.C. 154(b) by 407 days.

(21) Appl. No.: 13/054,534

(22) PCT Filed: Jul. 17, 2009

(86) PCT No.: PCT/AU2009/000918
§ 371 (c)(1),
(2), (4) Date: Feb. 17, 2011

(87) PCT Pub. No.: WO2010/006380
PCT Pub. Date: Jan. 21, 2010

(65) Prior Publication Data
US 2011/0137246 A1 Jun. 9, 2011

(30) Foreign Application Priority Data
Jul. 17, 2008 (AU) .............................. 2008903652

(51) Int. Cl.
*A61M 5/00* (2006.01)
(52) U.S. Cl.
USPC ........................................................ 604/110
(58) Field of Classification Search
USPC .................................................. 604/110, 218
See application file for complete search history.

(56) References Cited

U.S. PATENT DOCUMENTS

| 1,948,388 | A | * | 2/1934 | Liberson ..................... 604/183 |
| 4,659,330 | A |   | 4/1987 | Nelson et al. |
| 4,966,592 | A | * | 10/1990 | Burns et al. ................. 604/198 |
| 5,084,018 | A | * | 1/1992 | Tsao ........................... 604/110 |
| 5,195,982 | A |   | 3/1993 | Hoenig |
| 5,295,975 | A | * | 3/1994 | Lockwood, Jr. .............. 604/198 |
| 5,487,732 | A | * | 1/1996 | Jeffrey ......................... 604/110 |

(Continued)

FOREIGN PATENT DOCUMENTS

| EP | 1442763 | 8/2004 |
| JP | S625357 A | 1/1987 |

(Continued)

OTHER PUBLICATIONS

International Search Report; PCT/AU2009/000918; Oct. 1, 2009.

(Continued)

*Primary Examiner* — Nicholas Lucchesi
*Assistant Examiner* — Diva K Chander
(74) *Attorney, Agent, or Firm* — Cantor Colburn LLP

(57) ABSTRACT

A syringe including a barrel for containing a fluid, a needle associated with the barrel and in fluid communication therewith, a first plunger adapted to be contained at least partially within the barrel and movable relative thereto, a second plunger located at least partially externally to the barrel and movable relative thereto wherein the first plunger is releasably engaged with the second plunger, and wherein depression of the second plunger moves the first plunger to expel fluid contained within the barrel, and further depression of the second plunger frees the first plunger for movement relative to the second plunger from a use condition to a storage condition in which the needle is wholly contained within the barrel.

18 Claims, 8 Drawing Sheets

(56) References Cited

U.S. PATENT DOCUMENTS

| | | | |
|---|---|---|---|
| 5,788,677 A * | 8/1998 | Botich et al. | 604/195 |
| 6,387,078 B1 * | 5/2002 | Gillespie, III | 604/181 |
| 6,595,979 B1 * | 7/2003 | Epstein et al. | 604/506 |
| 7,175,609 B1 * | 2/2007 | Gray | 604/171 |
| 7,329,238 B2 * | 2/2008 | Halseth et al. | 604/110 |
| 7,458,962 B2 * | 12/2008 | McWethy et al. | 604/506 |
| 8,021,335 B2 * | 9/2011 | Lesch, Jr. | 604/135 |
| 8,128,605 B2 * | 3/2012 | Masi et al. | 604/240 |
| 8,152,778 B2 * | 4/2012 | Chebator | 604/231 |
| 2004/0087907 A1 | 5/2004 | Smith et al. | |
| 2004/0122375 A1 * | 6/2004 | Woodard et al. | 604/218 |
| 2005/0096597 A1 * | 5/2005 | Crawford et al. | 604/198 |
| 2005/0159705 A1 | 7/2005 | Crawford et al. | |
| 2009/0124970 A1 * | 5/2009 | Shue et al. | 604/110 |

FOREIGN PATENT DOCUMENTS

| | | |
|---|---|---|
| JP | 3047979 U | 4/1998 |
| JP | 2003516794 A | 5/2003 |
| WO | 200174428 | 10/2001 |
| WO | 2007104091 | 9/2007 |

OTHER PUBLICATIONS

Chinese Search Report; Chinese Application No. 2009801335122; Chinese Application Filing Date Jul. 17, 2009; Report Issued Aug 10, 2012.

Japanese Office Action for corresponding application JP2011-057715: Issued on Sep. 17, 2013.

* cited by examiner

DETAIL A

DETAIL B

RETRACTABLE SYRINGE

FIELD OF THE INVENTION

The present invention relates to a syringe. More specifically, the present invention relates to a syringe wherein a puncture needle may be retracted to prevent a sharps hazard.

BACKGROUND ART

With the ever-increasing awareness of needlestick injury and the risks associated with sharing needles, there have been many syringes introduced in the marketplace having some form of retractable needle. There are three basic types.

The first type can be seen as a "manual"-type syringe where, as the plunger is moved forwardly towards the end of the syringe barrel, it couples with a needle holder which contains the needle. The plunger can then be manually retracted which causes the needle to be retracted into the syringe body.

The second type can broadly be classified as "shoot back" syringes. In these syringes, some form of spring is provided. As the plunger is pushed forwardly towards the end of the syringe barrel, the needle holder is released and the spring causes the needle holder (containing the attached needle) to shoot back, either into the plunger body or into the syringe body. The spring may be mounted about the needle holder and under permanent compression until the needle holder is released. Alternatively, it is known to provide a spring that stretches as the plunger is pushed forwardly towards the front of the syringe barrel.

The third type can be broadly classified as "suck back" syringes. In these syringes, a reduced pressure (vacuum) is typically provided in the plunger and the front of the plunger is sealed by a piston. The piston is releasably mounted to the front of the plunger. The front of the syringe barrel has a releasable needle holder which contains the needle. As the plunger is pushed forwardly towards the end of the syringe barrel, the piston couples to the needle holder and at the same time, the piston is released from the front of the plunger and the needle holder is released from the front of the syringe barrel which causes the needle holder/piston to be sucked back into the plunger by the vacuum.

There are many variations to these three basic constructions. For instance, it is known to provide a "vacuum on demand" to the plunger which means that the syringe can be at atmospheric pressure until just before use at which stage a vacuum can be created in the plunger.

In each of the basic constructions, great care needs to be taken that the plunger (which may include a piston) properly couples to the needle holder such that the needle holder (containing the contaminated needle) can be properly retracted.

With a manual retraction, it is undesirable that a situation can occur where retraction of the plunger does not cause retraction of the needle holder.

With a shoot back mechanism, it is highly undesirable that the mechanism "triggers" at the wrong time, either too soon or too late. If the mechanism triggers too soon, there may still be appreciable medicine in the syringe which will be lost or wasted if the needle shoots back prematurely. Alternatively, it is also highly undesirable if the mechanism does not trigger when the plunger is pushed fully forwardly, or where it is necessary to place undue force on the plunger (which can damage the shoot back mechanism).

With a "suck back" mechanism, it is also highly undesirable that the mechanism triggers too soon or too late. With this type of mechanism, because the plunger is under vacuum, if the piston on the front of the plunger releases too early, the piston can be retracted (sucked back) into the plunger body without properly attaching to the needle holder. Alternatively, it is equally undesirable that the needle holder is released too early.

However, the particular construction of the single use syringes is such that tight tolerances in the triggering mechanism are required in order to ensure as much as possible, the correct action at the desired time, and these tight tolerances can lead to triggering problems, particularly as the syringes decrease in size, for example, in 1 ml syringes. Thus, the possibility of the release mechanism triggering either too late or too soon is ever present in this type of syringe, but is particularly acute in smaller syringes.

One cause for the premature triggering of the release mechanism is that the plunger needs to engage with the retraction device almost immediately upon the plunger being pushed into a forward part of the syringe. Thus, if the engagement does not occur immediately, malfunctioning of the release mechanism is more likely.

Another cause for premature triggering or delayed triggering is due to the particular manner in which the needle holder (often also called a luer) is attached in a releasable manner to the front of the barrel. It is known to hold the needle holder in a releasable manner to the front of the barrel using frictional engagement, and when the plunger is pushed towards the front of the barrel, the plunger engages with the needle holder to reduce the frictional engagement to such an extent that the needle holder can then be triggered to the retracted position. It is found that a frictional engagement of the needle holder to the barrel is not necessarily an entirely satisfactory arrangement.

Therefore, it is also known to provide a step or shoulder in the front of the barrel against which the needle holder is temporarily held until its release is triggered. It is therefore necessary to push the step or shoulder away to release the needle holder. It is also known to provide some form of "shatter plate" which is broken to release the needle holder, or some form of frangible portion. While some of these arrangements can provide a satisfactory temporary attachment of the needle holder in place, the manufacture of the step or shoulder in the front of the barrel can be quite difficult, again particularly in smaller syringes.

Some attempts have been made to overcome these problems. Applicant's own International Patent Application No. PCT/AU2007/000299, the disclosure of which is hereby incorporated by reference, discloses a needle containing medical device having a retractable needle.

Notwithstanding this potential solution, it would be an advantage to provide a retractable syringe having an improved design by which a needle hub can be released from the front of a syringe barrel.

In addition, it would be an advantage to provide a retractable syringe wherein the risk of needlestick injury to a user may be reduced prior to use of the syringe.

It will be clearly understood that, if a prior art publication is referred to herein, this reference does not constitute an admission that the publication forms part of the common general knowledge in the art in Australia or in any other country.

Throughout this specification, the term "comprising" and its grammatical equivalents shall be taken to have an inclusive meaning unless the context of use indicates otherwise.

OBJECT OF THE INVENTION

It is an object of the present invention to provide a retractable syringe which may overcome at least some of the above-mentioned disadvantages, or provide a useful or commercial choice.

In one aspect, the invention resides broadly in a syringe including a barrel for containing a fluid, a needle associated with the barrel and in fluid communication therewith, a first plunger adapted to be contained at least partially within the barrel and movable relative thereto, a second plunger located at least partially externally to the barrel and movable relative thereto wherein the first plunger is releasably engaged with the second plunger, and wherein depression of the second plunger moves the first plunger to expel fluid contained within the barrel, and further depression of the second plunger frees the first plunger for movement relative to the second plunger from a use condition to a storage condition in which the needle is wholly contained within the barrel.

The syringe of the present invention provides numerous significant advantages over the prior art. By providing a mechanism whereby a further depression of the second plunger once the fluid has been dispensed from the barrel results in retraction of the needle, the syringe can be quickly and effectively made safe (i.e. the chance of needlestick injury is reduced, if not eliminated) for medical or healthcare workers. In addition, the mechanism can be activated while the needle is still in the patient, meaning that there is no need to withdraw the needle from the patient first. This not only reduces the risk of needlestick injury but also reduces the risk of spraying (aerosoling) potentially contaminated bodily fluids or residual medications within the syringe if the retraction mechanism is activated externally to the patient's body.

The barrel of the present invention may be of any suitable type and fabricated from any suitable material. However, in a preferred embodiment of the invention, the barrel is fabricated from plastic. In some embodiments of the present invention, the barrel comprises a elongate member, and preferably a hollow elongate member (for instance, a hollow tubular member open at both ends). In this embodiment of the invention, one end of the barrel is typically tapered and may be sealed by the needle hub while the other end of the barrel may be sealed by the first plunger.

In a further embodiment of the invention, the barrel may be provided with locating means adapted to locate and retain the second plunger. The locating means may be of any suitable form, although it is preferred that the locating means is provided on an external surface of the barrel. A particularly preferred locating means is at least one extension standing proud of the surface of the barrel with a corresponding depression or opening on the second plunger.

In some embodiments of the present invention, the barrel may be provided with one or more indicia. Preferably, the one or more indicia are provided on an outer surface of the barrel. Any suitable indicia may be used (numbers, letters, symbols, pictures or the like, or any combination thereof), although in a preferred embodiment of the invention, the one or more indicia may relate to the volume of the barrel. In particular, the one or more indicia may be placed at one or more points on the barrel to indicate the volume of fluid contained within the barrel at that point.

In a preferred embodiment of the invention, the position of the second plunger relative to the indicia may be used to allow the use to determine the volume of fluid contained within the barrel.

The type of needle associated with the barrel is not critical. However, it is preferred that the needle is in the form of a puncture needle capable of puncturing the skin of a patient in order to allow the contents of the barrel to be dispensed either subcutaneously or intravenously. As the needle is in fluid communication with the barrel, the contents of the barrel will normally be transferable from the barrel to the patient through the needle or vice versa.

In a preferred embodiment of the invention, the needle is associated with a needle hub. Preferably, the needle is fixedly connected to the needle hub. The needle hub is preferably a portion of larger dimension than the needle and is adapted to attach or seal the needle to the barrel and/or first plunger.

In some embodiments of the invention, the barrel may comprise at least one locating means adapted to temporarily locate the needle hub relative to the barrel. The at least one locating means may comprise any suitable form. However, it is preferred that the at least one locating means may include a projection, such as a flange, adapted to, at least temporarily, prevent movement of the needle hub relative to the barrel when the syringe is in a use condition.

The at least one locating means is preferably provide at a forward end of the barrel. Typically, the forward end of the barrel tapers inwardly with the free end of the barrel defining an opening to releasably receive a portion of the needle hub. The needle hub is preferably provided with a circumferential shoulder portion which engages the free end of the barrel to hold the needle hub. The tapered portion of the barrel will typically be resilient to a small degree as it will normally be manufactured of plastic. Deformation of the tapered portion, normally outwardly, will preferably release the needle hub.

In a further embodiment of the invention, the needle hub may be provided with sealing means. The purpose of the sealing means is to provide a seal between at least a portion of the needle hub and an inside surface of the barrel in order to prevent fluid escaping from the barrel apart from through the needle. In addition, another purpose of the sealing means may be to prevent contaminants from entering the barrel and contaminating the fluid contained therein.

Any suitable sealing means may be used, such as, but not limited to, one or more O-rings, bungs, gaskets or the like. In one embodiment of the invention, the sealing means may comprise one or more toroidal members adapted to surround at least a portion of the needle hub in order to create a seal between the needle hub and an inner surface of the barrel.

The first plunger of the present invention may be of any suitable form. In some embodiments of the invention, the first plunger may comprise a stem, the stem being formed from one or more parts.

In a preferred embodiment of the invention, the first plunger may be provided with an engagement portion at a forward end thereof to engage the needle hub. The engagement portion may be of any suitable form, although it is preferred that the engagement portion is adapted to engage with the needle hub such that the needle hub and the first plunger may move relative to the barrel when the syringe transitions between a use condition (that is, before the contents of the barrel have been dispensed, and during the dispensing of the contents of the barrel), and a storage condition (that is, after the contents of the barrel have been dispensed).

The engagement of the engagement portion of the first plunger and the needle hub preferably may also result in the release of the needle hub from the locating means located on the barrel. Thus, when the portion of the first plunger and the needle hub are engaged, the needle hub is no longer engaged with the barrel.

Normally the engagement means will be an annular opening with a surrounding wall into which at least a portion of the needle hub can be received during engagement.

Preferably, the first plunger is associated with plunger sealing means, the plunger sealing means located at least partially within the barrel. The plunger sealing means may be of any suitable form, however it is preferred that the plunger sealing means is of sufficient dimensions such that a seal is formed between the first plunger and an inner surface of the barrel in order to prevent fluid escaping from the barrel apart from through the needle. In addition, another purpose of the plunger sealing means may be to prevent contaminants from entering the barrel and contaminating the fluid contained therein. The plunger sealing means may be formed integrally with the first plunger or may be formed separately therefrom and adapted to connection thereto. Normally the plunger sealing means is provided at the forward end of the first plunger.

Any suitable plunger sealing means may be used, such as, but not limited to, one or more O-rings, bungs, gaskets or the like. In one embodiment of the invention, the plunger sealing means may comprise one or more toroidal members adapted to surround at least a portion of the first plunger in order to create a seal between the first plunger and an inner surface of the barrel. In some embodiments, the surface of the first plunger may be provided with one or more retention means (recesses, grooves or the like) adapted to retain the plunger sealing means thereon.

In a preferred embodiment of the invention, the first plunger may further comprise locking means to releasably lock the first plunger to a portion of the second plunger. The second plunger may be provided with one or more complementary retention portions adapted to releasably retain the locking means.

The locking means may be of any suitable form, such as, but not limited to, one or more lugs, flanges, projections, finger members or the like, or any combination thereof. In a preferred embodiment of the invention, the one or more retention portions of the second plunger may comprise one or more shoulders, land or the like adapted to retain the locking means thereon.

According to a preferred form, the locking means will be provided on a rear portion of the first plunger and include at least one divergent flanges seated in a circumferential shoulder on the second plunger. The barrel is typically provided with depression means at an appropriate position such that depression of the engaged first and second plungers will cause the locking means to engage the depression means to unseat the locking means.

Also preferably provided on a rear portion of the first plunger is a sealing means adapted to seal with an internal surface of the second plunger to define an enclosure in an upper portion of the second plunger.

The second plunger may be of any suitable form. However, in a preferred embodiment of the invention, the second plunger may comprise an elongate member. Preferably, the second plunger comprises an elongate tubular member. In a most preferred embodiment of the invention, the second plunger may be open at the forward end and closed at the opposite end.

In some embodiments of the invention, the closed end of the second plunger may be provided with means to assist the user in mechanically or manually depressing the second plunger. Such means may comprise any suitable form, such as, but not limited to, a thumb pad.

In a preferred embodiment of the invention, when the syringe is assembled and the first plunger and the second plunger are releasably engaged with one another, the first plunger will be at least partially retained within the second plunger. It is envisaged that the sealed enclosure is located between the rearmost portion of the first plunger and the closed end of the second plunger. Preferably, this enclosure is a region of relatively low pressure (e.g. lower than atmospheric pressure). In some embodiments of the invention, the enclosure will be under vacuum. In order to maintain a region of relatively low pressure, it is preferred that the first plunger comprises one or more low pressure sealing means adapted to form a seal between the first plunger and an inner surface of the second plunger. The low pressure sealing means may comprise any suitable form provided that the low pressure sealing means is capable of maintaining a pressure differential between the region of relatively low pressure and atmospheric pressure.

During use, a user applies pressure to the second plunger, thereby causing a movement of the engaged first and second plungers relative to the barrel. As previously mentioned, once fluid has been dispensed from the barrel, a further depression of the second plunger causes the first plunger to engage with the needle hub, and the needle hub to disengage from the barrel. In addition, this further depression of the second plunger results in disengagement of the first plunger from the second plunger by depressing the flanges of the first plunger, thereby releasing the engaged first plunger and needle holder for movement relative to both the barrel and the second plunger.

When the first plunger and the now-engaged needle holder become free to move, the region of relatively low pressure in enclosure of the second plunger forces the engaged first plunger and needle holder to retract or be sucked back into the low pressure region to the storage condition. In this way, the needle may be retracted so as to be contained entirely within the barrel of the syringe, eliminating (or at least reducing) the chance of needlestick injury.

As previously discussed, the barrel may contain one or more locating means adapted to locate and retain the second plunger on the barrel. In this embodiment of the invention, the one or more locating means may comprise one or more projections extending outwardly from the outer surface of the barrel. In a preferred embodiment of the invention, the one or more projections may further comprise one or more shoulders, lands, flanges, rings or the like, or any combination thereof, adapted to further secure the second plunger to the barrel.

In embodiments of the invention in which the locating means comprises one or more projections, the second plunger may be provided with one or more complementary slots or channels in which the one or more projections may be positioned. In this way, the second plunger may be retained on the barrel but be movable relative to the barrel is a single plane only.

In a preferred embodiment of the invention, the movement of the second plunger relative to the barrel is a sliding movement, although it will be understood that any suitable movement could be used.

In some embodiments of the invention, the syringe may be provided with retaining means. In these embodiments of the invention, the retaining means is preferably associated with the second plunger. More preferably, the retaining means is adapted to be located and retained on the second plunger.

The retaining means may be of any suitable size, shape or configuration. However, in some embodiment of the invention, the retaining means may comprise an annular member adapted to be located a one end of the second plunger. Preferably, the retaining means is adapted to be located at the end of the second plunger closest to the needle. In a preferred embodiment of the invention, the second plunger is shaped so as to receive the retaining means. For instance, the second plunger may be provided with one or more recesses, lands, channels, grooves or the like (or any combination thereof) in which the retaining means may be located and retained.

The retaining means may serve a number of important purposes. For instance, in embodiments of the invention in which the second plunger is provided with one or more slots or channels, the retaining means may serve to prevent the end of the second plunger from splaying by substantially surrounding the end of the second plunger.

In addition, locating the retaining means at the end of the second plunger may serve to prevent the first plunger from being removed from the syringe through the end of the barrel furthest from the needle.

Furthermore, the retaining means may be adapted to retain the needle cap in place over the needle during transportation and storage of the syringe. In this embodiment of the invention, it is preferred that the retaining means is adapted to project above the surface of the second plunger when located on the second plunger such that the needle cap may be retained on the retaining means.

In some embodiments of the invention, the retaining means may be provided with engagement means in the form of (for instance) one or more projections adapted to engage with the second plunger to assist in retaining the retaining means against the second plunger. Any suitable projections may be provided. In a preferred embodiment of the invention, the one or more projections may be located on an inner surface of the retaining means. In a most preferred embodiment of the invention, the outer surface of the second plunger may be provided with complementary engagement means adapted to engage with the engagement means provided on the retaining means.

In another aspect, the invention resides broadly in a syringe including a barrel for containing a fluid, a needle associated with the barrel and in fluid communication therewith, a first plunger adapted to be contained at least partially within the barrel and movable relative thereto, a second plunger located at least partially externally to the barrel and movable relative thereto, wherein the first plunger is adapted for releasable engagement with the second plunger, a cover adapted to cover at least a portion of the needle, the cover being releasably engaged with the second plunger prior to use, wherein drawing back the second plunger disengages the cover from the second plunger, subsequent depression of the second plunger expels fluid contained within the barrel, and further depression of the second plunger frees the first plunger for movement relative to the second plunger from a use condition to a storage condition in which the needle is wholly contained within the barrel.

A significant advantage is provided by this embodiment of the present invention, in that, along with the previously mentioned advantages, the ability to disengage the cover from the syringe merely by drawing back the plunger means that a user is not required to put their fingers or hands anywhere near the cover when removing it in preparation for use of the syringe. In this way, the risk of needlestick injury, as well as potential damage to the syringe from improper removal of the cover, may be reduced, if not eliminated.

The cover may be of any suitable form. In some embodiments of the invention, the cover may comprise a cap member adapted to cover at least the tip of the puncture needle. Preferably, the cover is put in place during the manufacture or packaging of the syringe and is removed just prior to use of the syringe.

In some embodiments of the invention, the cover may be adapted to be retained on the second plunger using any suitable technique. For instance, the cover may be provided with one or more cover retention means (e.g. lands, projections, grooves, channels, rings, clips or the like) adapted for communication with a complementary portion of the second plunger. Preferably, the complementary portion of the second plunger is located on an external surface of the second plunger.

In a preferred embodiment of the invention, the engagement between the cover and the second plunger is sufficient to prevent the accidental or unintentional removal of the cover, for instance during manufacture, distribution or storage of the syringe. However, it is envisaged that the engagement between the cover and the second plunger may be overcome by a relatively small movement of the second plunger relative to the barrel of the syringe. In this way, the second plunger may be slightly drawn back in order to remove the cover from the syringe.

It is envisaged that, when a user wishes to remove the cover in order to use the syringe, the user will angle the syringe slightly downwardly (i.e. so that the needle end of the syringe is located lower than the other end of the syringe). In this position, a slight movement of the second plunger relative to the barrel will cause the cover to "pop" off, or be disengaged entirely from the syringe without the user needing to put any part of their body in the vicinity of the needle in order to remove the cover.

In an alternative embodiment of the invention, the syringe may be provided with means which, once actuated, may produce a controlled movement of the second plunger. Preferably, the controlled movement of the second plunger is sufficient to disengage the cover from the second plunger.

In some embodiments of the invention, the syringe may be provided with retaining means. In these embodiments of the invention, the retaining means is preferably associated with the second plunger. More preferably, the retaining means is adapted to be located and retained on the second plunger.

The retaining means may be of any suitable size, shape or configuration. However, in some embodiment of the invention, the retaining means may comprise an annular member adapted to be located a one end of the second plunger. Preferably, the retaining means is adapted to be located at the end of the second plunger closest to the needle. In a preferred embodiment of the invention, the second plunger is shaped so as to receive the retaining means. For instance, the second plunger may be provided with one or more recesses, lands, channels, grooves or the like (or any combination thereof) in which the retaining means may be located and retained.

In some embodiments of the invention, the retaining means may be provided with engagement means in the form of (for instance) one or more projections adapted to engage with the second plunger to assist in retaining the retaining means against the second plunger. Any suitable projections may be provided. In a preferred embodiment of the invention, the one or more projections may be located on an inner surface of the retaining means. In a most preferred embodiment of the invention, the outer surface of the second plunger may be provided with complementary engagement means adapted to engage with the engagement means provided on the retaining means.

In a more particular aspect, the invention resides broadly in a syringe including:
  a) a barrel for containing a fluid;
  b) a needle hub adapted for releasable engagement within the barrel, the needle hub including a needle in fluid communication with the barrel;
  c) a first plunger adapted to be contained at least partially within the barrel, the first plunger having a stem, the stem having, at one end, an engagement portion adapted for engagement with the needle hub, and wherein engagement of the engagement portion with the needle hub results in the needle hub being released from its engagement with the barrel;
  d) a second plunger located at least partially externally to the barrel and movable relative thereto, the second plunger being adapted for releasable engagement with the first plunger, the second plunger comprising a hollow bore having an open end and a closed end;

wherein depression of the second plunger expels fluid contained within the barrel, and further depression of the second plunger causes the engagement portion of the first plunger to engage the needle hub, the further depression releasing the needle hub from the barrel and the first plunger from the second plunger, thereby freeing the first plunger and needle hub for movement relative to the second plunger from a use condition to a storage condition in which the needle is wholly contained within the barrel.

In some embodiments of the invention, the syringe may be provided with retaining means. In these embodiments of the invention, the retaining means is preferably associated with the second plunger. More preferably, the retaining means is adapted to be located and retained on the second plunger.

The retaining means may be of any suitable size, shape or configuration. However, in some embodiment of the invention, the retaining means may comprise an annular member adapted to be located a one end of the second plunger. Preferably, the retaining means is adapted to be located at the end of the second plunger closest to the needle. In a preferred embodiment of the invention, the second plunger is shaped so as to receive the retaining means. For instance, the second plunger may be provided with one or more recesses, lands, channels, grooves or the like (or any combination thereof) in which the retaining means may be located and retained.

In some embodiments of the invention, the retaining means may be provided with engagement means in the form of (for instance) one or more projections adapted to engage with the second plunger to assist in retaining the retaining means against the second plunger. Any suitable projections may be provided. In a preferred embodiment of the invention, the one or more projections may be located on an inner surface of the retaining means. In a most preferred embodiment of the invention, the outer surface of the second plunger may be provided with complementary engagement means adapted to engage with the engagement means provided on the retaining means.

It is envisaged that the syringe of the present invention could be used for any suitable syringe size or volume. In addition, it is envisaged that the syringe of the present invention could be used for any suitable duty, such as dispensing any suitable fluid (such as a medication) or collecting fluids such as blood.

BRIEF DESCRIPTION OF THE DRAWINGS

An embodiment of the invention will be described with reference to the following drawings in which.

DETAILED DESCRIPTION OF THE DRAWINGS

Figure 1:
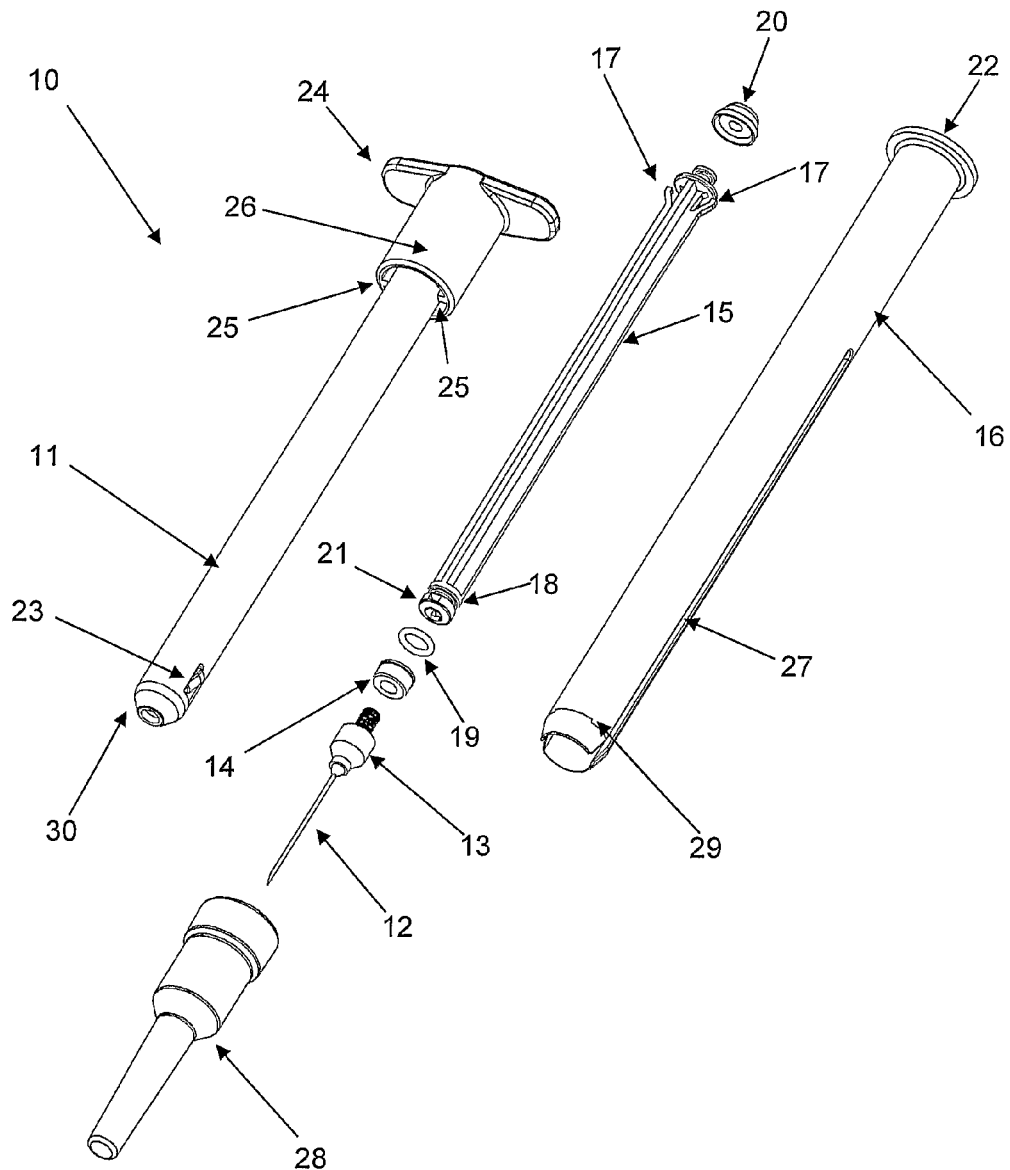
FIG. 1 illustrates an exploded view of a syringe according to an embodiment of the present invention.

It will be appreciated that the drawings have been provided for the purposes of illustrating preferred embodiments of the present invention and that the invention should not be considered to be limited solely to the features as shown in the drawings.

In FIG. 1 an exploded view of a syringe 10 according to an embodiment of the present invention is illustrated. The syringe 10 comprises a barrel 11, a puncture needle 12 fixedly connected to a needle hub 13, and a needle hub sealing means 14 in the form of a toroidal seal. The needle hub sealing means 14 is adapted to fit over a portion of the needle hub 13 and create a seal between the needle hub 13 and an inner surface of the barrel 11.

The syringe further comprises a first plunger 15 adapted to be contained at least partially within the barrel 11 and a second plunger 16 adapted to be retained at least partially externally to the barrel 11.

The first plunger 15 is an elongate member having locking means 17 adjacent one end. The locking means 17 are adapted to releasably lock the first plunger 15 to an inner surface of the second plunger 16. A groove 18 is provided in the surface of the first plunger 15 such that plunger sealing means 19 in the form of an O-ring may be connected to the first plunger 15 and form a seal between the first plunger 15 and the inner surface of the barrel 11. In addition, a vacuum seal 20 is adapted for connection to the first plunger 15 so as to form a seal between the first plunger 15 and an inner surface of the second plunger 16.

The first plunger is provided with a engagement portion 21 such that, when the second plunger 16 is depressed (by applying pressure to thumb pad 22) beyond the point at which all fluid has been expelled from the barrel 11, the engagement portion 21 is adapted to engage with the rear end of the needle hub 13. This further depression of the second plunger 16 results in the needle hub 13 being released from the needle hub locking means 23 located on the barrel 11, thereby freeing the needle hub 13 for movement relative to the barrel 11.

The barrel 11 further comprises locating means 24 adapted to locate and retain the second plunger at least partially on the external surface of the barrel 11. The locating means 24 comprises a pair of projections 25 extending outwardly from the surface of the barrel 11 surrounded by a ring 26. In this way, the second plunger 16 may be retained on the barrel 11.

The second plunger 16 is provided with a pair of slots 27 in which the projections 25 are located when the syringe 10 is assembled. In this way the second plunger 16 may be free to move relative to the barrel 11.

The syringe 10 further comprises a cover in the form of a needle cap 28. The needle cap 28 is adapted to be located over the needle 12 during transportation and storage to prevent injury to a person or damage to the needle 12. The needle cap 28 is retained on the second plunger 16 by engaging the needle cap 28 with one or more ridges 29 on the outer surface of the second plunger 29. The engagement between the needle cap 28 and the ridges 29 is sufficient to prevent the needle cap 28 from being removed during transport or storage of the syringe 10. However, even a relatively small movement of the second plunger 16 away from the needle end 30 of the barrel 11 will be sufficient to disengage the needle cap 28 from the ridges 29 and cause the cap 28 to "pop" off the syringe 10, thereby exposing the needle 12 in preparation for use of the syringe 10.

Figure 2:
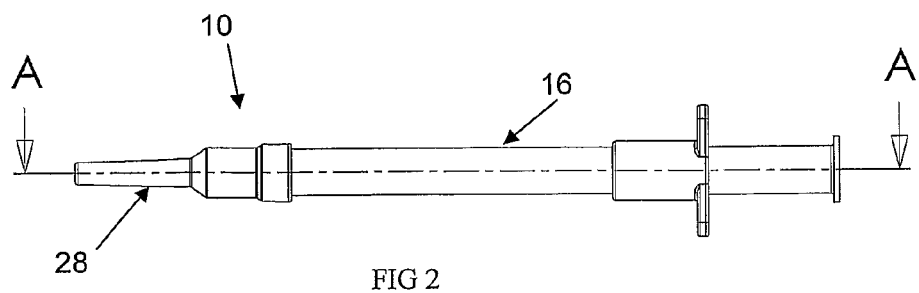
FIG. 2 illustrates a side elevation of a syringe according to an embodiment of the present invention.

In FIG. 2, a syringe 10 according to an embodiment of the invention is shown. The syringe 10 is shown in its state prior to use with the needle cap 28 in place and engaged with the second plunger 16.

Figure 3:
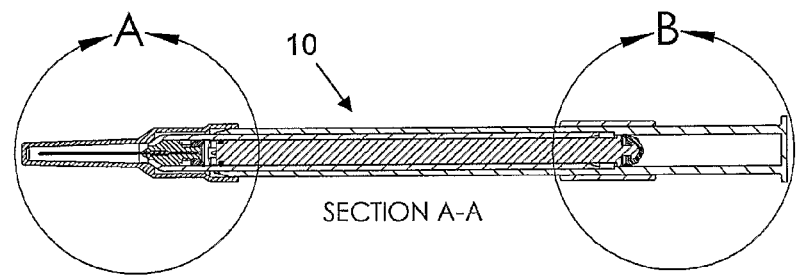
FIGS. 3-5 illustrate cross-sectional views of a syringe according to an embodiment of the present invention.

In FIG. 3 a cross-sectional view of the syringe 10 illustrated in FIG. 2 is shown. The portion of the syringe 10 designated by section A is illustrated in FIG. 4 while the portion of the syringe 10 designated by section B is illustrated in FIG. 5.

Figure 4:
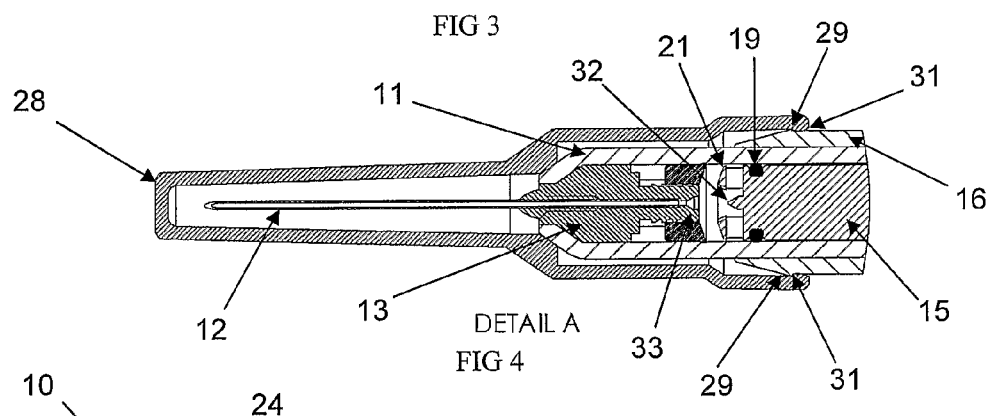
Figure 5:
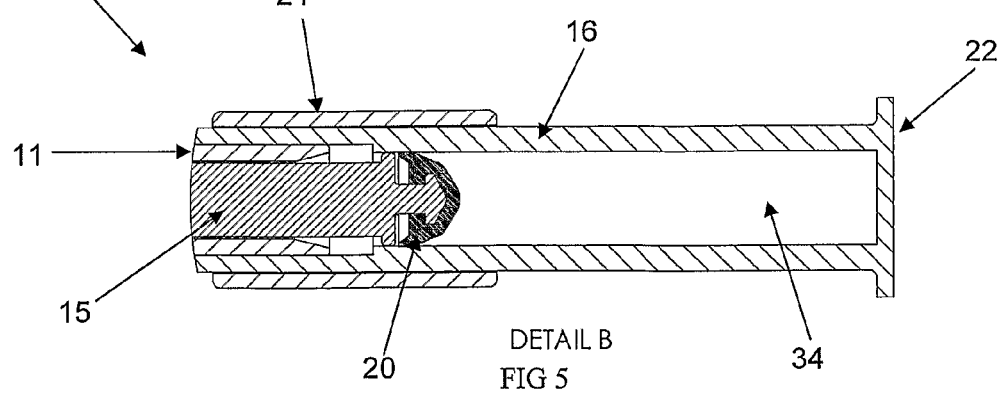

In FIG. 4, the needle 12 and needle hub 13 are shown when engaged with the barrel 11. The first plunger 15 is located substantially within the barrel 11 while the second plunger 16 is located substantially externally to the barrel 11. The needle cap 28 is positioned so as to entirely cover the needle 12, thereby preventing injury to a user or damage to the needle 12 prior to use.

The needle cap is provided with a ridge 31 which engages with a complementary ridge 29 provided on the outer surface of the second plunger 16. In this way, the needle cap 28 may be retained in position covering the needle 12 until such time as the second plunger 16 is mechanically or manually drawn back, releasing the engagement between the needle cap 28 and the second plunger 16.

It may be clearly seen in FIG. 4 that the first plunger 15 is provided with a seal 19 adapted to form a seal between the first plunger 15 and the inner surface of the barrel 11. In addition, the first plunger 15 is provided with a connection portion 21 comprising a projection 32 adapted to engage with a recess 33 in the rear of the needle hub 13. The engagement between the connection portion 21 and the needle hub 13 results in the release of the needle hub 13 from the barrel 11.

In FIG. 5, the rear end of the syringe 10 is shown. It may be seen that a low pressure region 34 exists in the gap between the rear of the first plunger 15 and the thumb pad 22 of the second plunger 16. The first plunger 15 is provided with a vacuum seal 20 adapted to form a seal between the first plunger 15 and an inner surface of the second plunger 16, thereby ensuring the pressure in the low pressure region 34 is maintained at sub-atmospheric levels.

It may be seen in this Figure that the second plunger 16 is located substantially externally to the barrel 11. However, the barrel 11 is provided with locating means 24 adapted to locate and retain the second plunger 16 on the outer surface of the barrel 11.

Figure 6:
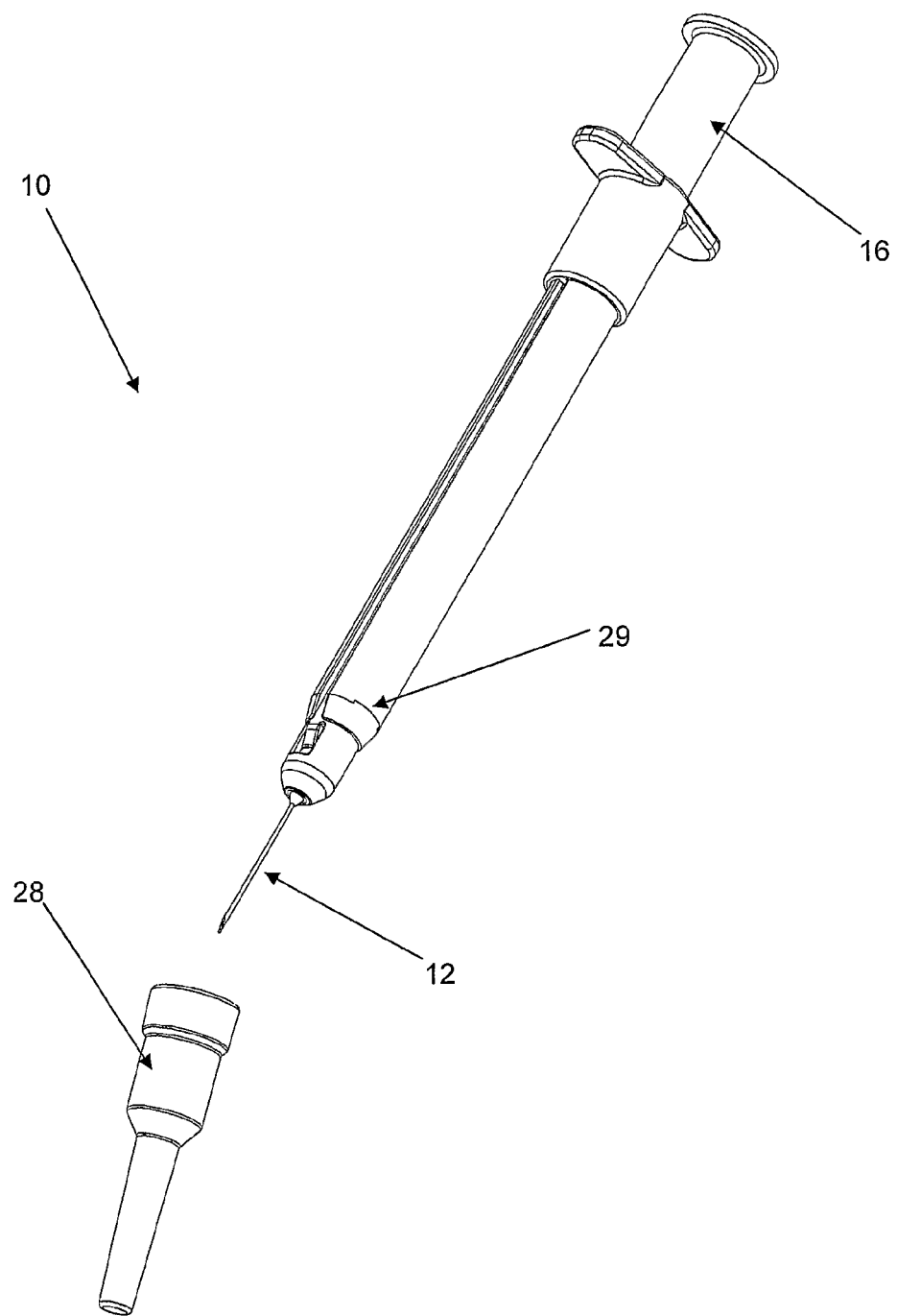
FIG. 6 illustrates a perspective view of a syringe according to an embodiment of the present invention.

In FIG. 6 the syringe 10 is shown when being prepared for use. In this Figure a user (not shown) angles the front of the syringe 10 (i.e. the end having the needle 12) downwardly and then draws the second plunger 16 back slightly. This retraction of the second plunger 16 results in the needle cap 28 disengaging from the ridges 29 on the second plunger 16. Due to the front of the syringe 10 being angled downwardly, the disengagement of the needle cap 28 from the second plunger 16 causes the needle cap 28 to fall off the syringe 10. It is envisaged that a user may wish to stand directly over a bin, tray, or the like when carrying out this step so that the needle cap 28 may be disposed of without the user having to handle the needle cap 28 or put their hands or fingers in the vicinity of the needle 12.

Figure 7:
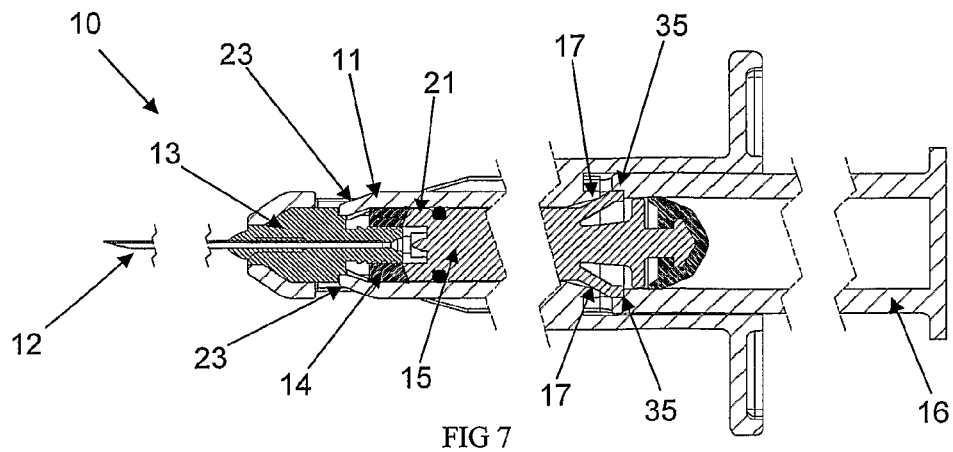
FIGS. 7-9 illustrate cross-sectional views of a syringe according to an embodiment of the present invention when in use.
Figure 8:
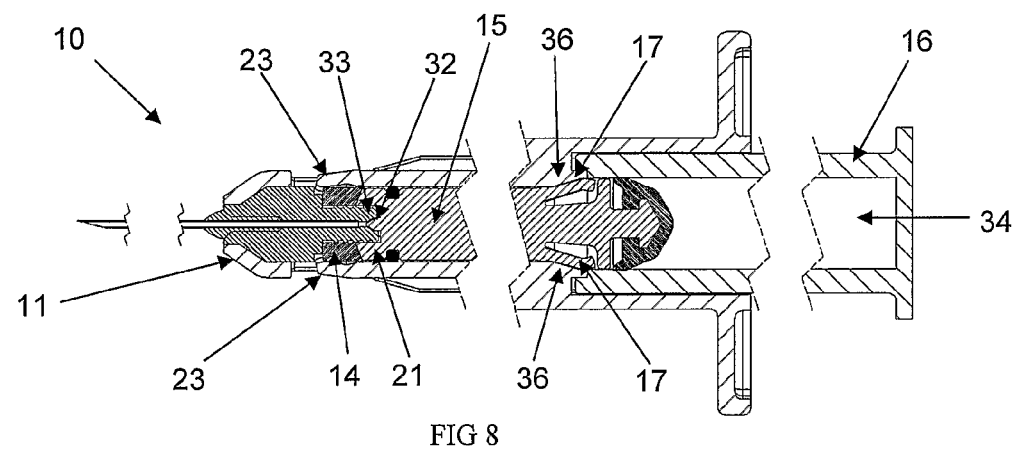
Figure 9:
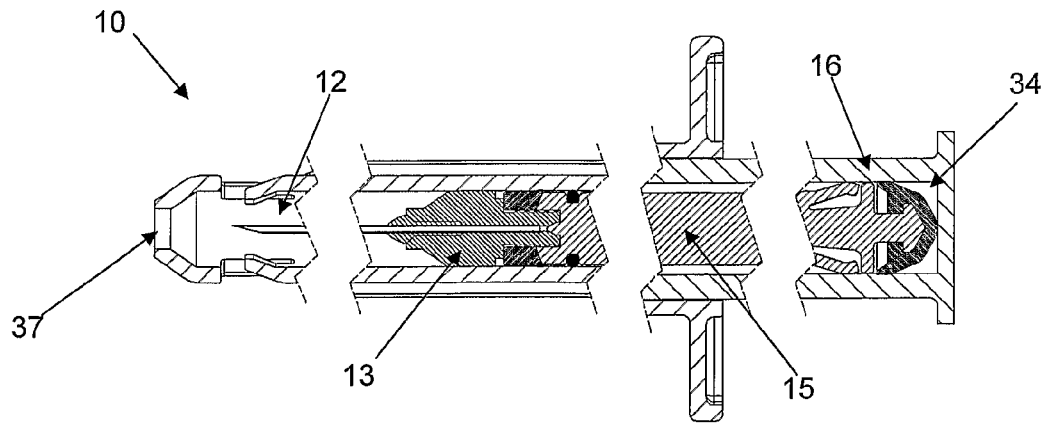

In FIGS. 7 to 9, the sequence of steps for the use of the syringe 10 according to an embodiment of the present invention are illustrated.

In FIG. 7, the second plunger 16 has been pushed forward, thereby dispensing all of the fluid contained in the barrel 11 out through the needle 12. In this position, the engagement portion 21 of the first plunger 15 abuts the needle hub seal 14. The locking means 17 provided on the first plunger 15 are locked in position against a shoulder 35 located on the inner surface of the second plunger 16.

In addition, the needle hub 13 is locked against movement relative to the barrel 11 by the needle hub locking means 23.

In FIG. 8, the second plunger 16 has been depressed further, thereby causing activation of the release mechanism. In this Figure, the further depression of the second plunger 16 results in the engagement portion 21 of the first plunger 15 pushing the needle hub seal 14 towards the front of the barrel 11. This movement of the needle hub seal 14 causes the needle hub seal 14 to force the needle hub locking means 23 to move outwardly, thereby unlocking the needle hub 13 from the barrel 11, freeing the needle hub 13 for movement relative to the barrel 11.

In addition, the further depression of the second plunger 16 forces the projection 32 associated with the engagement portion 21 of the first plunger 15 to engage with the recess 33 in the rear of the needle hub, thereby engaging the needle hub 13 with the first plunger 15.

Substantially simultaneously, the further depression of the second plunger 16 brings the locking means 17 of the first plunger 15 into abutment with a shoulder 36 of the barrel 11. The orientation of the shoulder 36 forces the locking means 17 to move inwardly, thereby releasing the locking means 17 from the second plunger 16.

Thus, in FIG. 8, the engaged needle hub 13 and first plunger 15 are now released from the barrel 11 and second plunger 16 respectively and are released for movement relative to the barrel 11. Movement of the engaged needle hub 13 and first plunger 15 relative to the barrel is achieved by the sucking back of the engaged needle hub 13 and first plunger 15 into the low pressure region 34 in the second plunger 16.

In FIG. 9, the engaged needle hub 13 and first plunger 15 have been sucked back into the low pressure region 34 in the second plunger 16. Thus, the syringe 10 is now in the storage condition. In this condition, the needle 12 is contained entirely within the barrel 11, meaning that a user is unlikely to receive a needlestick injury. In addition, the retraction mechanism of the present invention significantly reduces, and if not eliminates, the likelihood of aerosoling of medication or bodily fluids from the opening 37 in the end of the barrel 11 as the needle 12 retracts into the barrel 11. Also the fact that the low pressure region 34 is maintained at a lower pressure than atmospheric pressure means that the engaged needle hub 13 and first plunger 15 will not move relative to the barrel 11 once retracted into the storage condition.

Figure 10:
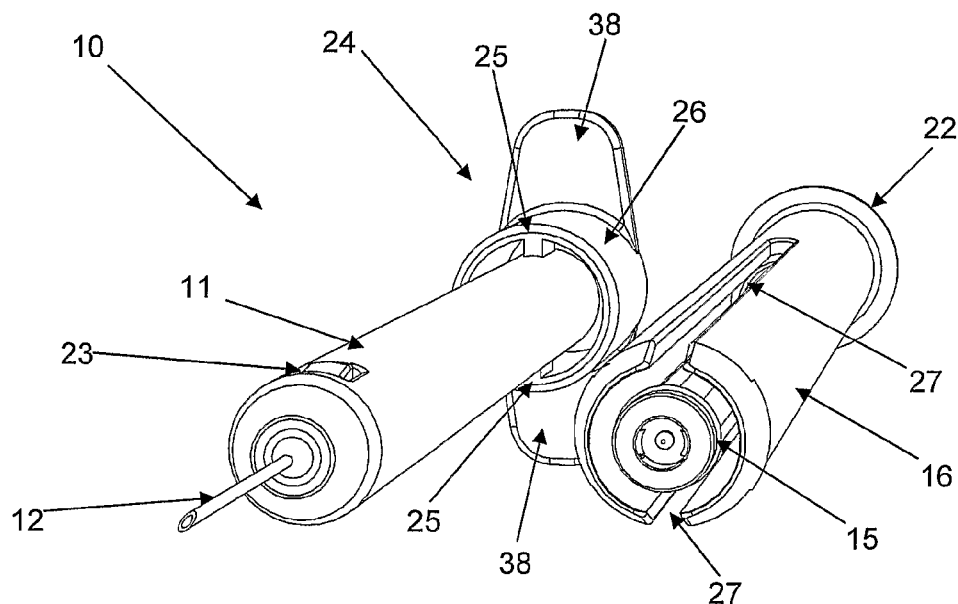
FIGS. 10-11 illustrates perspective views of a syringe according to an embodiment of the present invention.
Figure 11:
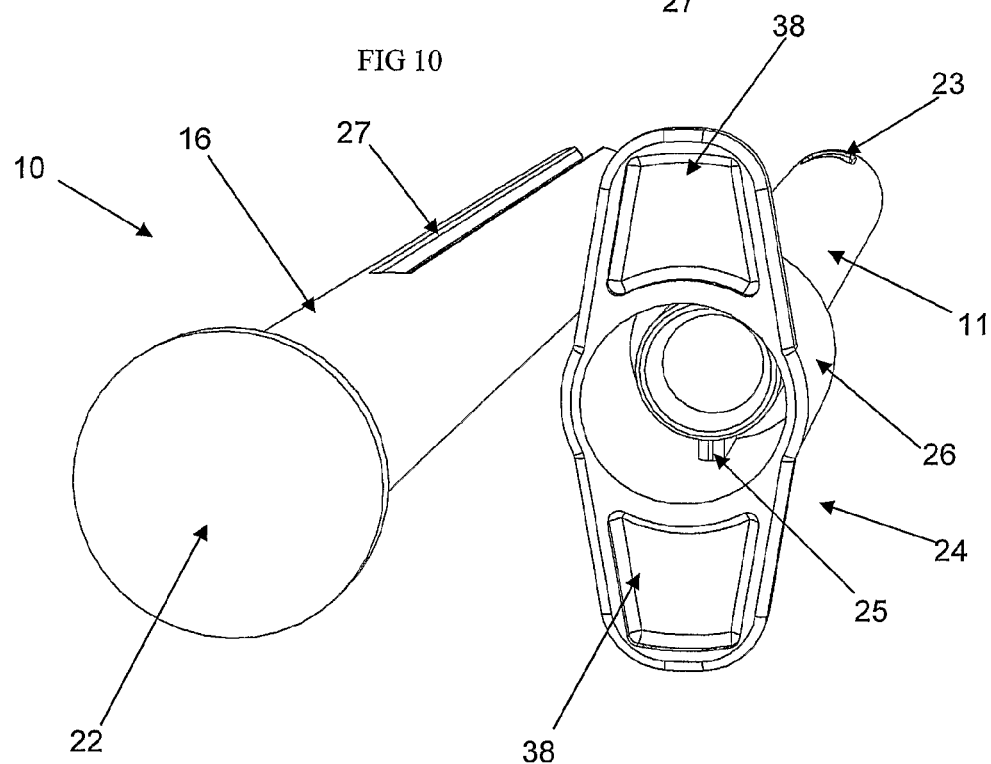

In FIGS. 10 and 11, perspective views of the syringe 10 according to an embodiment of the present invention are illustrated. In these Figures the barrel 11 may be seen with the needle 12 projection through an open end of the barrel 11. The needle hub locking means 23 may also be clearly seen. The locating means 24 in the form of a pair of projections 25 associated with a ring 26 of material may be seen. The pair of projections 25 serve to locate the second plunger 16 on the external surface of the barrel 11, while the ring 26 ensures that the second plunger 16 is retained on the barrel 11. The locating means 24 is also provided with a pair of lands 38. In use, a user may place their fingers on the lands 38 and then depress the thumb pad 22 of the second plunger 16.

The first plunger 15 may also be seen when locked to the second plunger 16. In addition, the slots 27 in the second plunger 16 in which the projections 25 of the locating means 24 are located when the syringe 10 is in use may be clearly seen.

Figure 12:
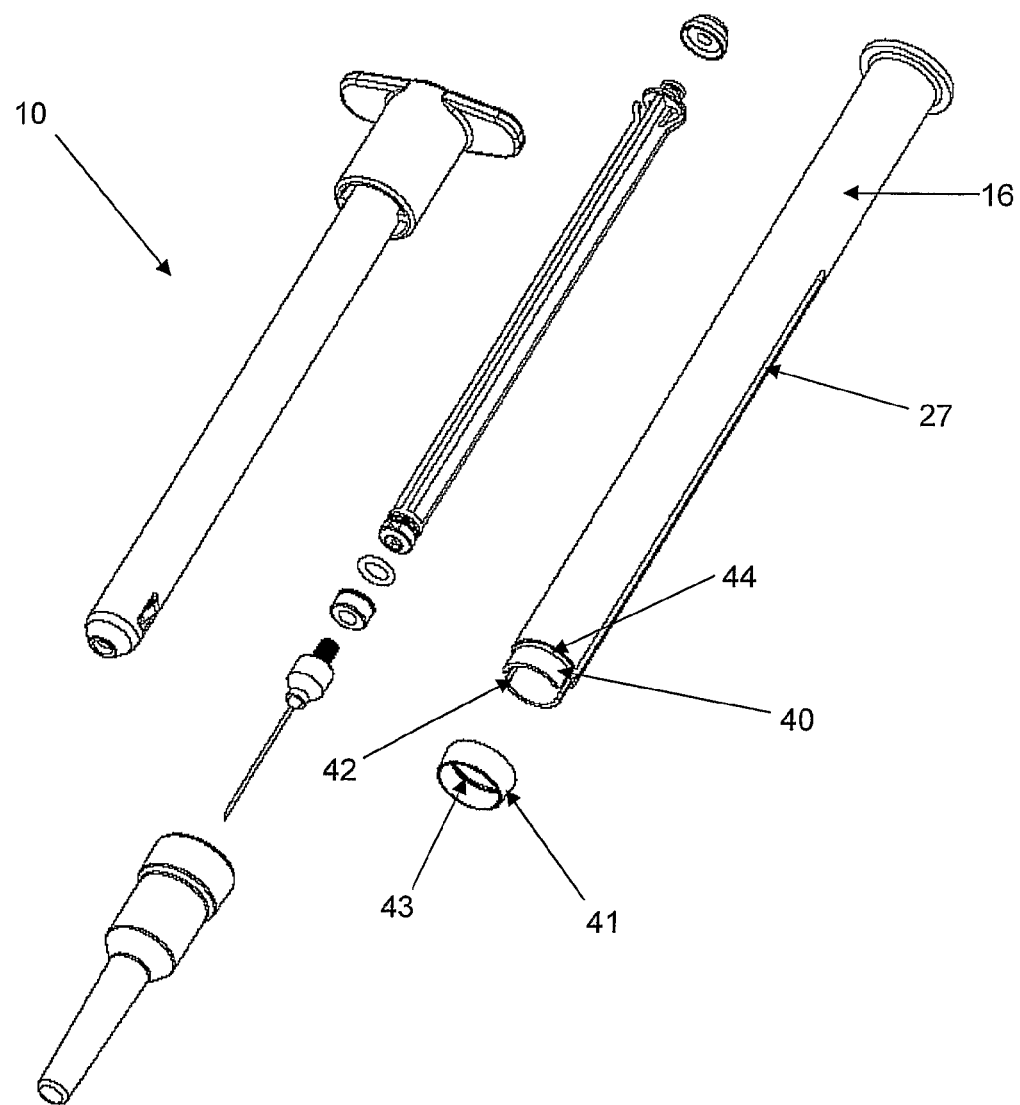
FIG. 12 illustrates an exploded view of a syringe according to an alternative embodiment of the present invention.

In FIG. 12, an exploded view of a syringe 10 according to an alternative embodiment of the invention is illustrated. The syringe 10 shown in FIG. 12 is identical to that shown in FIG. 1 in many ways, with the exception that the second plunger 16 is provided with a recessed region 40 adjacent the needle end 42 of the second plunger 16. Retaining means in the form of an annular ring 41 is adapted to be located and retained on the recessed region 40.

Locating the annular ring 41 on the recessed region 40 ensures that the slots 27 that extend along the second plunger 16 are unable to splay at the needle end 42 of the second plunger 16 due to the presence of the annular ring 41.

It may be seen in this Figure that the inner surface of the annular ring 41 is provided with engagement means in the form of an annular projection 43 adapted to engage with complementary engagement means in the form of a channel 44 located on the recessed region 40. The engagement between the annular projection 43 and the channel 44 assists in retaining the annular ring 41 against the surface of the second plunger 16.

Figure 13:
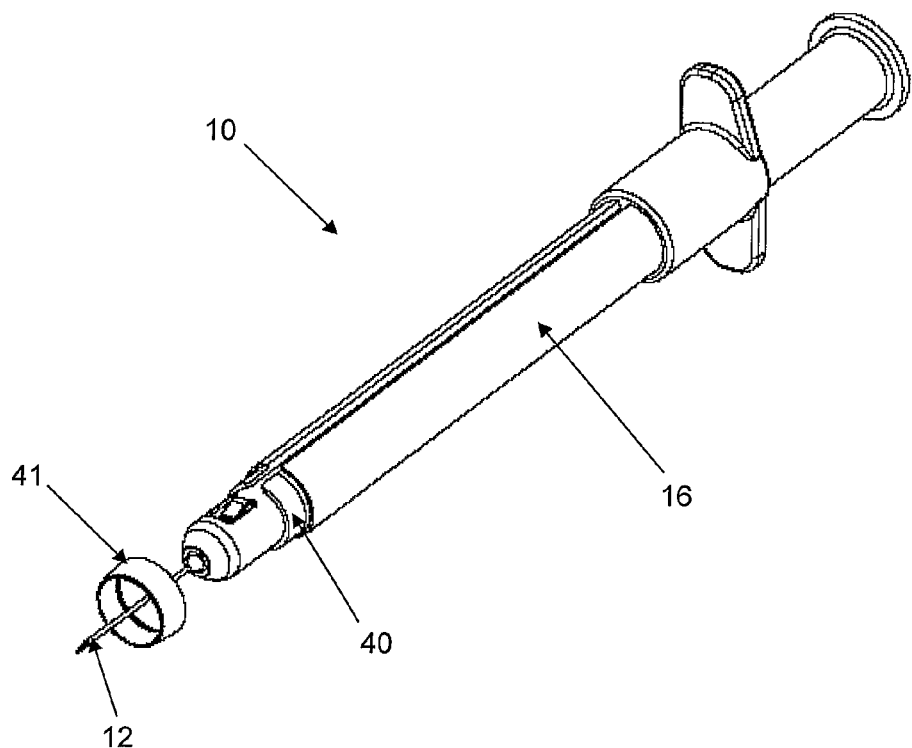
FIG. 13 illustrates a perspective view of a syringe according to an alternative embodiment of the present invention.

In FIG. 13, a perspective view of a syringe 10 according to an alternative embodiment of the invention is shown. This Figure illustrates the manner in which the annular ring 41 slips over the needle 12 in order to be located and retained in place on the recessed region 40 of the second plunger 16.

Figure 14:
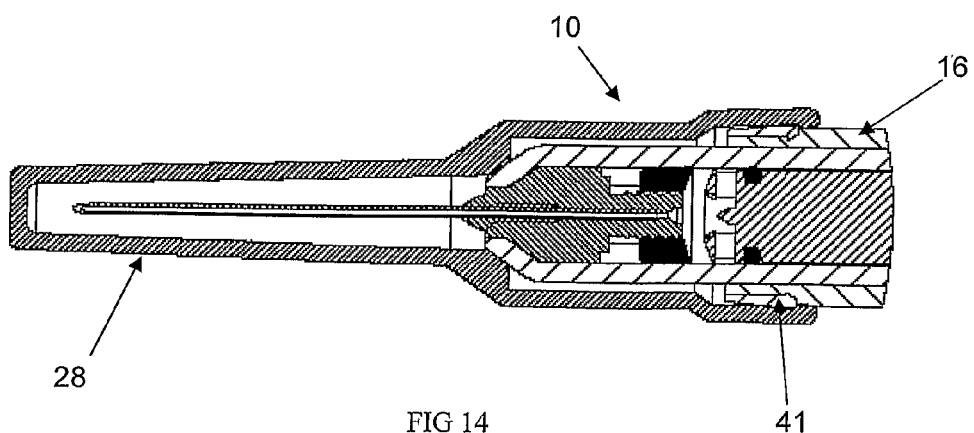
FIG. 14 illustrates a cross-sectional view of a syringe according to an alternative embodiment of the present invention.

In FIG. 14, a cross-sectional view of a syringe 10 according to an alternative embodiment of the present invention is shown. In this Figure it may be seen that the annular ring 41 is adapted to project slightly above the outer surface of the second plunger 16, thereby providing a land or projection on which the needle cap 28 is retained when the syringe 10 is being transported or stored.

Figure 15:
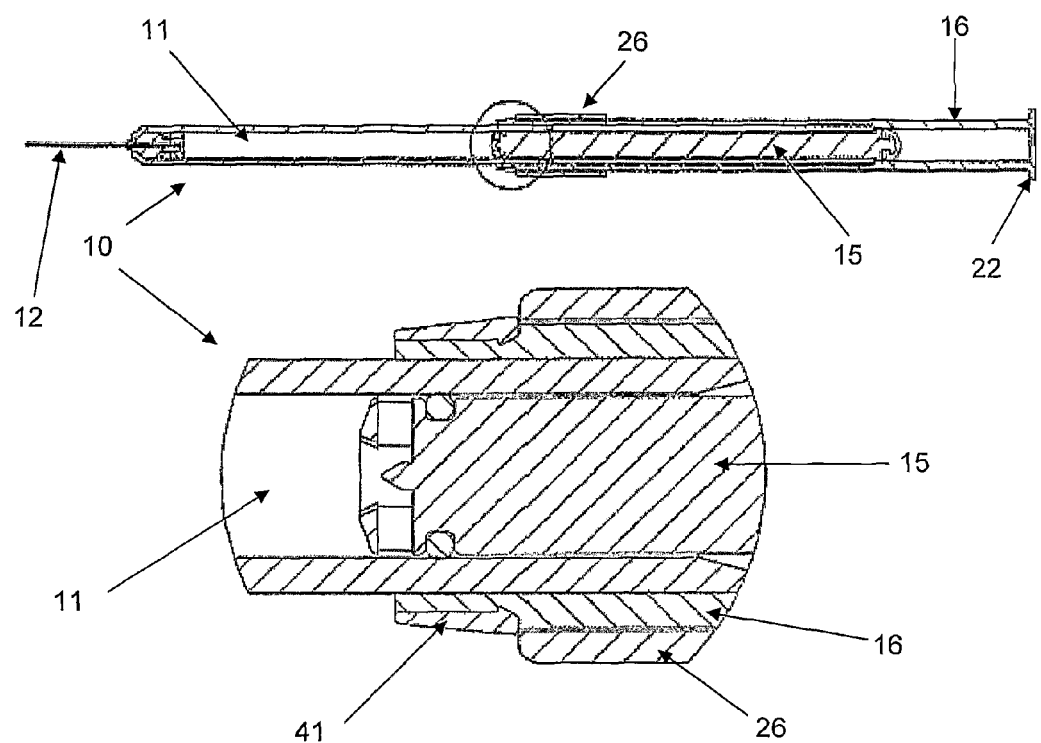
FIG. 15 illustrates a detailed cross-sectional of a syringe according to an alternative embodiment of the present invention.

In FIG. 15, a detailed cross-sectional view of a syringe 10 according to an alternative embodiment of the present invention is shown. It may be seen in this Figure that as the first plunger 15 and the second plunger 16 are drawn back (for instance, when drawing medication into the barrel 11 of the syringe 10, the first plunger 15 will be prevented from being removed from the barrel 11 through the end of the barrel furthest from the needle 12 (i.e. to the right in FIG. 15). The removal of the first plunger 15 is prevented due to the presence of the annular ring 41 that is adapted to project slightly above the outer surface of the second plunger 16. As the first plunger 15 and second plunger 16 are drawn back, the projecting portion of the annular ring 41 abuts the ring 26 provided on the barrel 11, thereby preventing any further movement of the first 15 and second 16 plungers from left to right in FIG. 15. This in turn prevents the first plunger 15 from being entirely withdrawn from the barrel 11 through the end of the barrel furthest from the needle 12 and closest to the thumb pad 22 (i.e. to the right in FIG. 15).

Those skilled in the art will appreciate that the present invention may be susceptible to variations and modifications other than those specifically described. It will be understood that the present invention encompasses all such variations and modifications that fall within its spirit and scope.

The invention claimed is:

1. A syringe including
a barrel for containing a fluid,
a needle associated with the barrel and in fluid communication therewith,
a first plunger adapted to be contained at least partially within the barrel and movable relative thereto,
a second plunger located at least partially externally to the barrel and movable relative thereto
wherein the first plunger is releasably engaged with the second plunger, and
wherein depression of the second plunger moves the first plunger to expel fluid contained within the barrel, and further depression of the second plunger frees the first plunger for movement relative to the second plunger from a use condition to a storage condition in which the needle is wholly contained within the barrel.

2. A syringe according to claim 1 wherein the barrel is a hollow elongate member sealed at a first end by a needle hub.

3. A syringe according to claim 2 wherein the needle is fixedly connected to the needle hub.

4. A syringe according to claim 1, wherein the barrel is provided with locating means on an outer surface thereof, the locating means being adapted to locate and retain the second plunger.

5. A syringe according to claim 4 wherein the locating means comprise one or more projections adapted to be positioned within one or more slots or channels provided on the second plunger.

6. A syringe according to claim 1, wherein the first plunger comprises locking means adapted to releasably lock the first plunger to a portion of the second plunger.

7. A syringe according to claim 1, wherein the first plunger is provided with sealing means adapted to form a seal between the first plunger and an internal surface of the second plunger to define an enclosure in a rearmost portion of the second plunger.

8. A syringe according to claim 7 wherein the enclosure is a region of relatively low pressure.

9. A syringe according to claim 7 wherein when the first plunger retracts into the enclosure when the first plunger moves between the use condition and the storage condition.

10. A syringe according to claim 2 wherein the further depression of the second plunger causes the first plunger to engage with the needle hub.

11. A syringe according to claim 1, wherein the syringe is provided with retaining means located on the second plunger.

12. A syringe according to claim 11 wherein the retaining means is an annular ring.

13. A syringe according to claim 11 wherein the retaining means is adapted to project above the outer surface of the second plunger in order to prevent the withdrawal of the first plunger from the barrel through the end of the barrel furthest from the needle.

14. A syringe according to claim 1, wherein the syringe is provided with a cap that substantially covers the needle during transportation or storage.

15. A syringe according to claim 1, wherein the outer surface of the barrel is provided with indicia relating to the volume of the barrel.

16. A syringe including
a barrel for containing a fluid,
a needle associated with the barrel and in fluid communication therewith,
a first plunger adapted to be contained at least partially within the barrel and movable relative thereto,
a second plunger located at least partially externally to the barrel and movable relative thereto,
wherein the first plunger is adapted for releasable engagement with the second plunger, a cover adapted to cover at least a portion of the needle, the cover being releasably engaged with the second plunger prior to use,
wherein drawing back the second plunger disengages the cover from the second plunger, subsequent depression of the second plunger expels fluid contained within the barrel, and further depression of the second plunger frees the first plunger for movement relative to the second plunger from a use condition to a storage condition in which the needle is wholly contained within the barrel.

17. A syringe according to claim 16 wherein the cover is a needle cap.

18. A syringe including:
   a) a barrel for containing a fluid;
   b) a needle hub adapted for releasable engagement within the barrel, the needle hub including a needle in fluid communication with the barrel;
   c) a first plunger adapted to be contained at least partially within the barrel, the first plunger having a stem, the stem having, at one end, an engagement portion adapted for engagement with the needle hub, and wherein engagement of the engagement portion with the needle hub results in the needle hub being released from its engagement with the barrel;
   d) a second plunger located at least partially externally to the barrel and movable relative thereto, the second plunger being adapted for releasable engagement with the first plunger, the second plunger comprising a hollow bore having an open end and a closed end; wherein depression of the second plunger expels fluid contained within the barrel, and further depression of the second plunger causes the engagement portion of the first plunger to engage the needle hub, the further depression releasing the needle hub from the barrel and the first plunger from the second plunger, thereby freeing the first plunger and needle hub for movement relative to the second plunger from a use condition to a storage condition in which the needle is wholly contained within the barrel.

* * * * *